(12) United States Patent
Pariseau et al.

(10) Patent No.: US 6,541,260 B1
(45) Date of Patent: Apr. 1, 2003

(54) DEVICE FOR DETECTING AND INDICATING FLUID PROPERTIES

(76) Inventors: Blake Pariseau, 54 Marathon St., Apt. 2, Arlington, MA (US) 02474; Eric R. Muse, 40 Vernal St., Everett, MA (US) 02149

(*) Notice: Subject to any disclaimer, the term of this patent is extended or adjusted under 35 U.S.C. 154(b) by 9 days.

(21) Appl. No.: 09/838,352

(22) Filed: Apr. 19, 2001

(51) Int. Cl.[7] .............................................. G01N 33/14
(52) U.S. Cl. ............................ 436/24; 422/28; 422/29; 422/30; 422/31
(58) Field of Search ............................ 422/28, 29, 30, 422/31; 436/24

(56) References Cited

U.S. PATENT DOCUMENTS

| 3,544,484 A | | 12/1970 | Roth |
| 3,930,592 A | | 1/1976 | DiIanni |
| 4,166,804 A | | 9/1979 | Bleha et al. |
| 4,526,752 A | * | 7/1985 | Perlman et al. ............... 422/56 |
| 4,929,090 A | | 5/1990 | Grahm |
| 5,200,909 A | | 4/1993 | Juergens |
| 5,271,278 A | | 12/1993 | Salgues |
| 5,403,720 A | | 4/1995 | Sato et al. |
| 5,451,526 A | | 9/1995 | Cui et al. |
| 5,795,773 A | * | 8/1998 | Read et al. ............... 435/287.5 |
| 5,801,061 A | * | 9/1998 | Stephenson ............... 436/169 |
| 5,854,072 A | | 12/1998 | Dittrich et al. |
| 6,352,837 B1 | * | 3/2002 | Witcher et al. ............... 435/31 |
| 6,221,451 B1 | * | 4/2002 | Lauer et al. ............... 428/36.5 |

* cited by examiner

*Primary Examiner*—Jill Warden
*Assistant Examiner*—Sam P. Siefke
(74) *Attorney, Agent, or Firm*—O'Connell Law Firm

(57) ABSTRACT

A device for detecting and providing an indication regarding one or more properties of a fluid retained in a bottle comprising a body member and a fluid property detecting substance, which can test for acidity, cork taint, or another fluid property, operably associated with the body member for detecting and providing an optical indication regarding one or more properties of the fluid retained in the bottle. The body member can have an open inner volume and the fluid property detecting substance can be disposed therein. A wall portion of the body member can comprise a semi-permeable barrier for allowing a one-way flow of fluid retained in the bottle into the open inner volume of the body member.

21 Claims, 3 Drawing Sheets

DEVICE FOR DETECTING AND INDICATING FLUID PROPERTIES

FIELD OF THE INVENTION

The present invention relates generally to devices for indicating substance properties and characteristics. More particularly, disclosed herein is a device, such as a stopper, for detecting and indicating properties and characteristics of a fluid contained in a bottle.

BACKGROUND OF THE INVENTION

The taste of wine can be adversely affected in numerous ways. Some contaminating effects can take hold while the wine remains sealed in its bottle by a cork. Others tend to attack the taste quality of the wine only after the wine bottle has been opened as by removing the cork. In each case, however, it is difficult to perceive the taint visually. As a result, tasting is typically the only means by which one can hope to determine whether the wine has been tainted.

Of course, the typical consumer can open and taste wine only after he or she has actually purchased the bottle of wine and brought it home. Furthermore, certain types of wine taint are difficult to perceive or identify, particularly by the non-expert, even upon tasting. With this, even after tasting, the wine taster may merely find wine unsuitable for consumption or at least less than ideal in taste without being able to confirm with certainty that the wine is tainted or to discern particularly how the wine is tainted.

One unfortunately common type of wine taint is commonly referred to as cork taint, "corking" or being "corked." Corking can occur to varying degrees. Furthermore, threshold sensitivity to corking varies from individual to individual. As a result, one person may be able to perceive and identify corking in a given bottle while another person tasting the same wine might either not be able to identify how the wine is tainted or may not be able to perceive the taint at all. It is said that the most perceptive five per cent of the population are about 200 times more sensitive than the bottom five per cent. This is true not only with regard to cork taint but also with regard to other tainting effects.

The incidence of cork taint is sporadic and random. However, when it takes hold, it can be quite aggressive. Research has recorded the incidence of cork taint to vary between three and five per cent. It can strike any wine regardless of price or type. Since it takes effect after bottling, it cannot be detected until the bottle is opened. Cork taint manifests itself as very undesirable aroma and flavor characters that are imparted to bottled wines following contact with their cork. The chemical compound contributing most significantly to cork taint is 2,4,6 trichloroanisole or TCA, which is implicated in more than 80 per cent of cork tainted wines. However, at least five other compounds also can contribute to cork taint. They are guaiacol, geosmin, 2-methylisobomeol (MIB), octen-3-ol, and octen-3-one.

Aside from guaiacol, each compound is sensorially very potent. For example, research indicates that TCA can be detected in dry white wine and sparkling wines at levels of roughly two parts per trillion, which approximately equals 0.000000000002 grams in a liter of wine, and in red and port wines at around five parts per trillion. Some of the other compounds have sensory thresholds of approximately 20 parts per trillion. When so bad as to be readily perceptible, TCA typically has a musty, moldy or wet Hessian character. MIB and geosmin have an earthy/muddy aroma; guaiacol is smoky or medicinal; and octen-3-ol and octen-3-one are said to smell of tinned mushrooms.

The production of TCA is the result of rather complex chemical mechanisms. The most fundamental of these is the conversion of chlorophenols to chloroanisole by common microscopic fungi and possibly yeasts and bacteria in the presence of moisture. Unfortunately, chlorophenols have been used as pesticides and as wood preservatives. Consequently, they are common environmental pollutants. The uptake of even minute amounts of chlorophenol by the bark of a cork tree at any stage during its growth can yield corks that will produce cork taint in wine. The same is true if the cork is exposed to chlorophenols during manufacture. Also, cork taint can be the result of an interaction of TCA from the moulds naturally occurring in the tree bark, with chlorine, a chemical used to sanitize the cork. To be complete, one will note that, for similar reasons, TCA can be a major contaminant of many other foods and beverages.

In practice, whether corking will actually infect a bottle of wine depends on a plurality of factors. Among those factors are the fit in the bottleneck, the corking device clamp, and the quality and dimensions of the cork. Of these, the most important issue is the quality of the cork. In bottled wine, glass is the only inert element. The cork is not. As such, it is subject to attack by moths and moulds, which are the natural inhabitants of corks. The dominant types of moulds in long-life corks are Aspergillum and Penicillium. Moulds are naturally present in corks at bottling while the presence of yeasts and bacteria in commercial corks is relatively infrequent.

There have been some attempts at improvements in cork processing and storage. For example, some practitioners have ceased using bleach as a cork treatment during processing, which is useful since, as was discussed above, the reaction of chlorine with a mold-produced compound is a major factor in TCA production. Unfortunately, even these practices have failed to eliminate cork taint.

Of course, a number of further factors beyond cork taint can affect the taste and quality of wine. For example, empty space between the cork and wine is necessary to absorb moderate thermal changes. However, where air occupies that empty space, an excessive amount of space will increase the oxidation of the wine while in the bottle while too little air space decreases the wine's ability to withstand temperature changes thereby causing regurgitations. To prevent this, most wine today is bottled without air in an inert atmosphere of nitrogen and carbon dioxide gas.

Another characteristic that can affect the taste and quality of wine is volatile acidity, which is commonly referred to as VA. Volatile acids include acetic acid, tartaric acid, malic acid, and others. Ethyl acetate is basically a sign of degradation in wine quality and is the dominant ester in numerous wines. It is held more responsible for the souring characteristic than acetic acid (vinegar) itself, and its perception threshold is estimated at being between 180 and 200 mg/l. VA's can be sensed, such as by one's nose, in the gas-occupied space above wine and by tasting since they are fixed in the wine. Many sources can give rise to these volatile components. Generally, however, they are the result of spoilage yeasts or bacteria that are allowed to proliferate in the wine. Once present, these are difficult to remove. Like many other characteristics of wine, VA's to varying degrees can be desired by some but disliked by others.

Still another potential factor affecting the taste and quality of wine is brettanomyces, which is a yeast. Brettanomyces is commonly indicated by the presence of 4-ethyl phenol and 4-ethyl guaiacol. Some wine drinkers disdain the presence of brettanomyces in wine while others find its taste pleasurable.

An even further component that can affect wine is acetaldehyde such that it may be termed aldehydic. It is common for sherry to be aldehydic. However, an acetaldehyde character in red or white wine is generally considered undesirable. This character can be nutty, musty, or swampy. Wines with this flaw have often been exposed to too much oxygen. To a limited degree, acetaldehyde can be desirable but can be unpleasant when excessive where the wine may simply be considered oxidized.

Hydrogen sulfide, commonly found in sewer gas and emitted by rotten eggs, results in wine from an inability of yeasts to deal properly with amino acid synthesis. It can also result from a reaction with sulfur, a common fungicide. Wine containing hydrogen sulfide is often referred to as being reduced. Mercaptans are closely related and are more garlicky or oniony in character. They are sulfur compounds and result from a reaction of ethanol in the wine with hydrogen sulfide.

From the foregoing, it will be clear that many of reactions and other effects can and do take hold of wine prior to opening. However, by exposing its contents to air, the opening of a bottle of wine typically triggers what may be considered a secondary fermentation and a far more rapid degradation of wine quality and taste. Even further, though, one will note that it is desirable to allow a wine to breathe for a given amount of time, such as a few minutes to as much as one or two hours, to allow for certain volatile components to be dispensed. Removal of such volatile components improves the taste and bouquet of wine.

Disadvantageously, with prolonged exposure to air, wine is subject to the effects of a number of reactions and contaminants including roughly 200 yeast spores. With this, exposure to ambient air causes oxidation with a consequent production of excessive acids and changes in the taste, aroma, and color of the wine. As a result, the contents must be consumed in a reasonably short period of time to prevent spoilage from rendering the wine unfit for consumption.

In light of the foregoing, one will appreciate that many factors can affect the taste and quality of wine. Some factors, such as excessive oxidation, can render a wine unfit for consumption by any person. Others, depending on the degree to which they have taken hold, can cause a wine to be desirable to one person yet undesirable to another person.

Unfortunately, at present, it appears that the determination of whether and to what degree a given effect has taken hold of a bottle of wine cannot be accomplished without the bottle's being opened and its contents examined. With this, a wine consumer must purchase or at least open the wine before he or she can even hope to determine, by way of example, whether corking has taken place or whether and to what degree brettanomyces is present in the wine. Furthermore, even when the bottle has been opened, determining whether wine is corked or the extent to which other substances are present in the wine typically requires tasting by one with an educated and sensitive palate or testing by relatively complex procedures.

With these things in mind, it has become apparent to the present inventors that it would be desirable to provide a device and method for enabling a wine consumer to perceive whether a volume of wine in a bottle has been affected by a given factor, such as cork taint, oxidation, or any one of a plurality of potentially detrimental or desirable factors. It would be still more desirable to provide such a method and device that could indicate, not only whether a given factor is present, but also the degree to which it has taken hold. Even more preferable would be a device and corresponding method that would allow a wine consumer to perceive simultaneously whether a plurality of different factors have taken place in wine and, if so, the extent to which the wine has been affected.

SUMMARY OF THE INVENTION

Advantageously, the present invention sets forth with the broadly stated object of providing a device for detecting and providing an indication regarding one or more fluid properties of a fluid retained in a bottle that solves each of the problems left by the prior art while providing a number of heretofore unrealized advantages thereover.

In achieving this object, one preferred embodiment of the present invention essentially comprises a body member and a fluid property detecting substance operably associated with the body member for detecting and providing an optical indication regarding one or more properties of the fluid retained in the bottle. The body member can have an open inner volume and the fluid property detecting substance can be disposed therein. A wall portion of the body member can comprise a semi-permeable barrier for allowing a one-way flow of fluid retained in the bottle into the open inner volume of the body member. Preferably, an outer wall of the body member will be translucent for enabling a user to view the optical indication provided by the volume of fluid property detecting substance.

The fluid property detecting substance can test for one or more of a plurality of properties including levels of acidity, cork taint, hydrogen sulfide, and additionally or alternatively brettanomyces yeast. Where cork taint is to be detected, the detecting substance can be calibrated to indicate the presence of excessive levels of 2, 4, 6 trichloroanisole (TCA), guaiacol, geosmin, 2-methylisoborneol (MIB), octen-3-ol, and/or octen-3-one.

The body member of the device can comprise a stopper with a generally cylindrical body portion for being disposed in a neck portion of the bottle. In such a case, the body portion can be formed by a first annular segment that is coupled to a second annular segment by a tubular member, and a plurality of annular fins can project from the tubular member for providing an improved seal between the body member and the neck portion of the bottle.

In an alternative embodiment, the stopper can have a body member formed of, for example, cork or a polymeric material. In this embodiment, the stopper can be impregnated with the fluid property detecting substance. In a still further refinement, the body portion can be divided into a plurality of sections. Each section can be impregnated with a fluid property indicating substance that is calibrated to test for and indicate a different property of the fluid retained by the bottle. With this, the plurality of sections of the stopper can be employed for detecting and indicating different types of properties, different levels of the same property, or both.

In yet another embodiment, the device can have an open inner volume divided into a plurality of wedge-shaped compartments, and each wedge-shaped compartment can retain a volume of fluid property indicating substance. With this, the fluid property indicating substance of each of the plurality of wedge-shaped compartments can be calibrated to test for and indicate a different property of the fluid retained by the bottle.

One will appreciate that the foregoing discussion merely outlines the more important features of the invention to enable a better understanding of the detailed description that follows and to instill a better appreciation of the inventor's contribution to the art. Before an embodiment of the invention is explained in detail, it must be made clear that the following details of construction, descriptions of geometry, and illustrations of inventive concepts are mere examples of the many possible manifestations of the invention.

DETAILED DESCRIPTION OF PREFERRED EMBODIMENTS

To ensure that one skilled in the art will fully understand and, in appropriate cases, be able to practice the present invention, certain preferred embodiments of the broader invention revealed herein are described below and shown in the accompanying drawing figures. It must be expressly noted, however, that the following exemplary embodiments are mere manifestations of an invention that is broader than any embodiment thereof.

Figure 1:
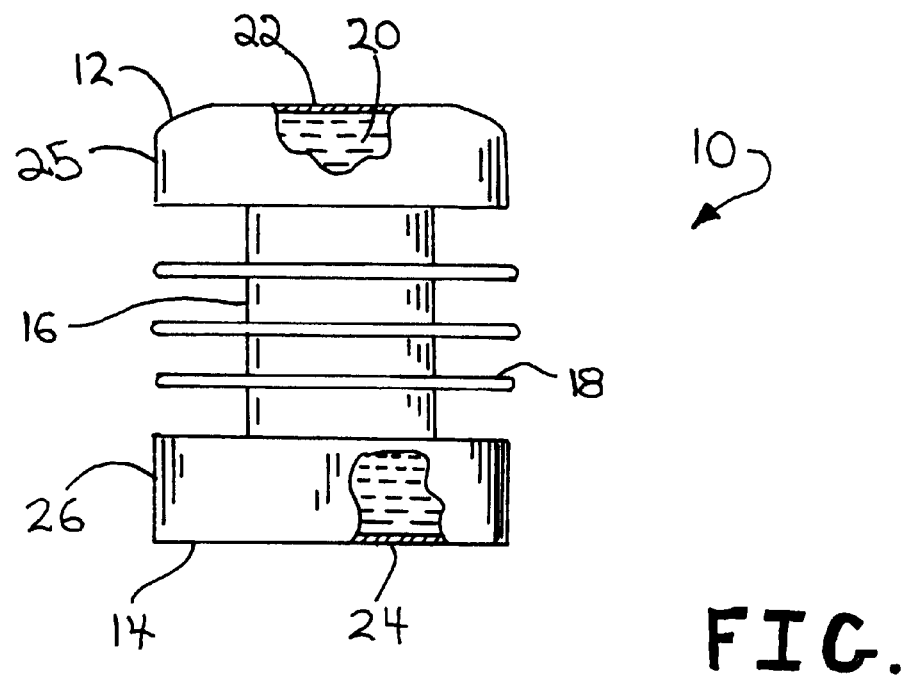
FIG. 1 is a view in side elevation of a stopper for detecting and indicating fluid properties according to the present invention.

Looking more particularly to the drawing figures, a first preferred embodiment of the present invention for a device for detecting and indicating fluid properties is indicated generally at 10 in FIG. 1. In the embodiment of FIG. 1, the device 10 comprises a stopper, which is also indicated at 10, that essentially comprises a generally cylindrical body that is formed by a first annular-segment 12 that is coupled to a second annular segment 14 by a tubular member 16. A plurality of annular fins 18 project from the tubular member 16.

The first annular segment 12 has a round outside wall 25 and a generally flat end wall 22. Likewise, the second annular segment 14 has an outside wall 26 and a generally flat end wall 24. In use, the stopper 10 will be installed in a bottle with the end wall 24 of the second annular segment 14 disposed adjacent to the inner volume of the bottle and, therefore, adjacent to or in contact with the liquid contents of the bottle and with the end wall 22 of the first annular segment 12 facing outwardly of the bottle.

As defined by the joined first and second annular segments 12 and 14 and the tubular member 16, the stopper 10 has a given overall length and a given effective outside diameter, which is determined by the outside diameters of the first and second annular segments 12 and 14 and the annular fins 18. Preferably, those outside diameters are substantially equal. Ideally, of course, the effective diameter of the stopper 10 is calibrated such that the stopper 10 will be frictionally retained in a bottle neck of, for example, a wine bottle (not shown) to be removed only by a withdrawing means, such as a wine screw or the like (not shown).

Advantageously, the first and second annular segments 12 and 14 and the tubular member 16 include an open inner volume. The open inner volume retains a volume of fluid property detecting substance 20 for providing an optical indication of, as its name would suggest, one or more properties of a fluid retained within, for example, the bottle that the stopper 10 is employed to seal. The fluid property detecting substance 20 could be liquid, solid, gas, powder, gel, or any other material that, as will be discussed more fully hereinbelow, could be employed for detecting spoilage or contamination in a liquid. Stated more particularly, depending on the goals of the user, the fluid property detecting substance 20 can be chosen, with regard to wine as the tested fluid, to indicate excessive levels of contamination, potentially objectionable levels of fermentation by-products, alcohol levels, excessive oxidation giving rise to high acidity, or any other fluid property that is subject to detection.

Preferably, the outside walls 25 and 26 of the first and second annular segments 12 and 14 are translucent and even more preferably transparent. Similarly, the end wall 22 of the first annular segment 12 is translucent, preferably transparent. Indeed, the entire shell of the stopper 10 as defined by the first and second annular segments 12 and 14 and the tubular member 16 can be transparent to enable a most convenient viewing of the fluid property detecting substance 20 within the open inner volume of the stopper 10. With this, a user can view optical indications provided by the fluid property detecting substance 20 both from the side and from the end of the stopper 10.

The preferred end wall 24 of the second annular segment 14 comprises a semi-permeable barrier, which is also indicated at 24. As a result, properties of the fluid retained within the open inner volume of the bottle can be detected by the fluid property detecting substance 20. Once detected, the properties of the fluid can be indicated by an optical indication from the fluid property detecting substance 20. With this, the user can perceive qualities of the fluid within the bottle without a need for opening the bottle or tasting the fluidic contents of the bottle.

By means that would be readily obvious to one skilled in the art after reading this disclosure, the semi-permeable barrier 24 is chosen to act as a one-way barrier. With this, the liquid to be tested can enter the open inner volume of the stopper 10 to interact as necessary with the fluid property detecting substance 20. However, the fluid property detecting substance 20 is blocked from escaping from the open inner volume of the stopper 10 to contaminate the liquid contents of the bottle relative to which the stopper 10 is secured. Although a number of possible material options for the semi-permeable barrier 24 exist, one possible option is a micro-porous polymer chosen and calibrated in light of the characteristics of the fluid property detecting substance 20 and the fluid to be tested.

Of course, the nature and composition of the fluid property detecting substance 20 will depend primarily on the property sought to be detected. One might reasonably assume that the property that would be sought to be detected for most commonly would be excessive acidity caused by oxidation. In such a case, the fluid property detecting substance 20 would preferably incorporate a substance that provides a chromatic indication of the presence of excessive acidity and would even more preferably comprise a chromatically-indicating acid and base indicator.

A logical choice for such an acid and base indicator would be a litmus material, such as a litmus solution, that would optically indicate the level of acidity of the liquid retained in the bottle. For example, the litmus solution could be calibrated to turn red if the retained liquid in the bottle is overly acidic and could be calibrated to turn blue if the retained liquid is overly alkaline. It should be clear, however, that the fluid property detecting substance 20 could by any one of a number of acid and hydronium ion testing substances that would be obvious to one skilled in the art in light of this disclosure. In any case, the preferred fluid property detecting substance 20 will be chosen or calibrated to demonstrate a color change at a predetermined level of acidity as determined to be unacceptably high by, for example, the producer of the liquid retained in the bottle.

It will again be noted, however, that acidity is not the only property that one might wish to detect in, for example, a bottle of wine. For example, the fluid property detecting substance 20 alternatively or additionally could be selected to provide an optical indication of cork taint. To do so, the fluid property detecting substance 20 can detect for the existence of 2, 4, 6 trichloroanisole (TCA), guaiacol, geosmin, 2-methylisoborneol (MIB), octen-3-ol, and/or octen-3-one, which each can evidence cork taint. However, since TCA is the most prevalent indicator of cork taint, the fluid property detecting substance 20 may be chosen to provide an optical indication of the existence of an excessive concentration of TCA, which can depend on the type of wine to be tested and on the tastes of the consumer. For example, the fluid property detecting substance 20 could indicate, for example, when the concentration of TCA exceeds 2 parts per trillion. The fluid property detecting substance 20 could also or alternatively test for the presence of excessive amounts of brettanomyces yeast and for excessive amounts of hydrogen sulfide.

Figure 2:
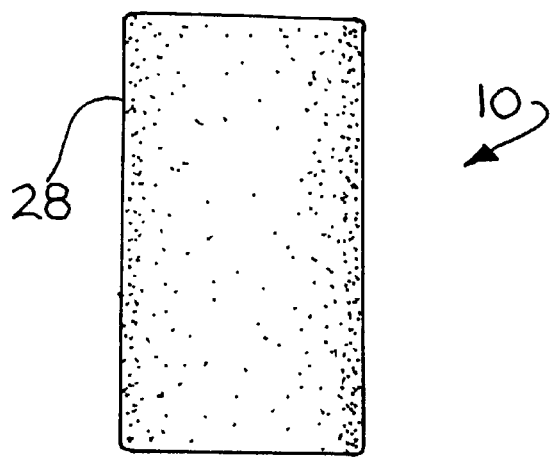
FIG. 2 is a view in side elevation of an alternative embodiment of the present invention for a stopper for detecting and indicating fluid properties.

It will be noted, however, that the stopper 10 could assume a plurality of other configurations and compositions that each would be well within the scope of the present invention. One such alternative configuration is shown in FIG. 2. There, the stopper 10 comprises an essentially unitary body 28, which may be formed from cork, a polymeric material, or substantially any other appropriate material. In this embodiment, the body 28 of the stopper 10 can act as a carrier that is impregnated or saturated with one or more indicator materials or dyes for providing a chromatic optical indication of a property or characteristic of a volume of fluid retained in a bottle or the like. Preferably, the indicator materials or dyes have reactive groups that produce a chemical bond with the carrier material of the body 28. Under such a construction, the stopper 10 can provide an optical indication of the selected characteristic or property of the fluid in the bottle thereby enabling a user to make a determination regarding that property without a need for opening the bottle.

Figure 3:
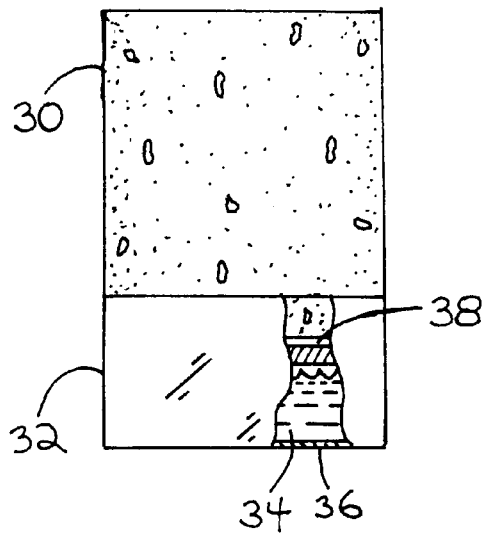
FIG. 3 is a partially sectioned view in side elevation of another alternative embodiment of the stopper for detecting and indicating fluid properties.

A further embodiment of the stopper 10 is shown in FIG. 3 where the stopper 10 is formed by the coupling of a body portion 30 with a property indicating portion 32. The body portion 30 again could be formed from cork, a polymeric material, or any one of a plurality of other suitable stopper materials. The property indicating portion 32 has a sealed open inner volume that retains a volume of fluid property detecting substance 34. The property indicating portion 32 also includes a cup portion 38 that matingly receives an end of the body portion 30. The property indicating portion 32 and the body portion 30 are secured together by friction, adhesive, or any other appropriate means. In a manner similar to the embodiment of FIG. 1, a semi-permeable barrier 36 acts as an end wall for the stopper 10 to enable fluid properties to be detected by the fluid property detecting substance 34. With this, a user can ascertain properties and characteristics of a fluid retained in a bottle by review of the color condition of the fluid property detecting substance 34 through the bottle neck and the ideally transparent outer wall of the property indicating portion 32.

Figure 4:
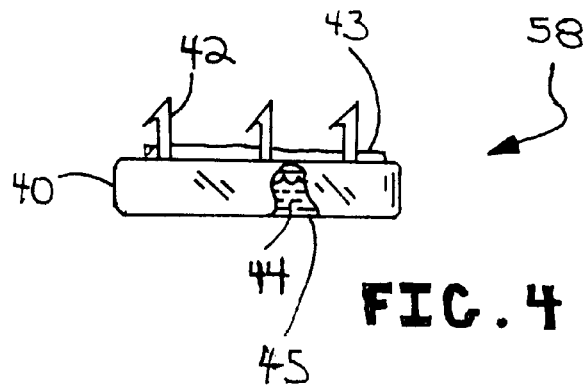
FIG. 4 is a partially sectioned view in side elevation of yet another embodiment of the present invention for a device for detecting and indicating fluid properties.

It should be appreciated, however, that the present invention need not comprise an entire stopper 10 as FIGS. 1–3 have shown. For example, as is depicted in FIG. 4, the invention could be embodied in an annular property indicating member 58 that can be coupled to a standard stopper (not shown). As such, the property indicating member 58 can comprise a hollow body with an open inner volume housing a volume of fluid property detecting substance 44, with a transparent outer wall 40, and a semi-permeable barrier 45. Still further, a plurality of retaining prongs 42 project from the property indicating member 58 from the side opposite the semi-permeable barrier 45 such that the prongs 42 can be embedded in a standard stopper to couple the property indicating member 58 thereto. The property indicating member 58 can additionally or alternatively be secured to the standard stopper by adhesive 43. Under this arrangement, substantially any stopper can be fitted with the property indicating member 58, and properties of the fluid contained within the bottle can be determined visually by a user.

Figure 5:
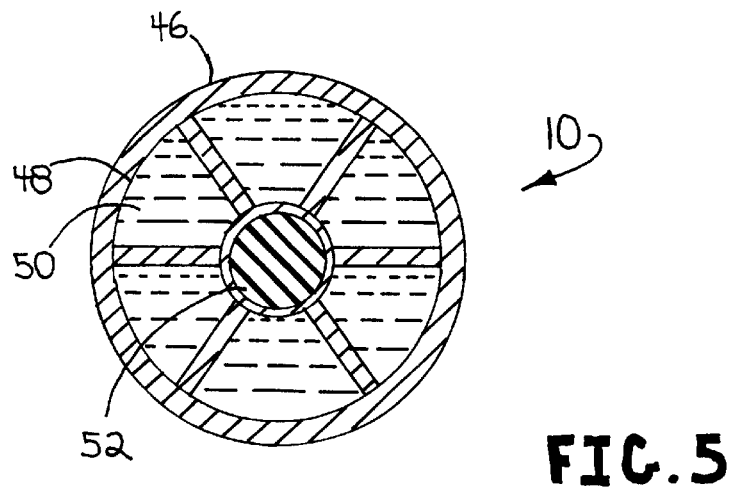
FIG. 5 is a cross-sectional plan view of still another alternative embodiment of the present invention.

Although the abovedescribed embodiments may be quite complete for many purposes, the inventors advantageously have appreciated that it may be preferable in certain circumstances to provide a stopper 10 that can provide indications regarding a plurality of different fluid properties simultaneously. An embodiment of the invention that can achieve such a goal is indicated generally at 10 in FIG. 5. There, the stopper 10 is shown in cross section to have a cylindrical outer wall 46, which is preferably transparent. The inner volume of the stopper 10 is divided into a plurality of wedge-shaped compartments 48. Each wedge-shaped compartment 48 retains a volume of fluid property indicating substance 50. Also, a central plug 52 is disposed in a middle portion of the stopper 10 for allowing the stopper 10 to receive and be removed by, for example, a wine screw or the like (not shown).

Under this arrangement, the fluid property indicating substance 50 of each of the plurality of wedge-shaped compartments 48 can be chosen and calibrated to test for and indicate a different property of the fluid retained by a bottle with which the stopper 10 is used. For example, a first wedge-shaped compartment 48 can test for and indicate a relative acidity level of the retained liquid. Also, a second wedge-shaped compartment 48 can test for and indicate excessive levels of cork taint in the liquid retained by the bottle. Still further, a third wedge-shaped compartment 48 can test for and indicate the presence of excessive levels of brettanomyces yeast. Even further still, a fourth wedge-shaped compartment 48 can provide a chromatic indication as to whether excessive levels of hydrogen sulfide are present in the fluid retained by the bottle. Any remaining wedge-shaped compartments 48 can be used for indicating regarding still further contaminating or otherwise taste-affecting characteristics.

Alternatively or additionally, the plurality of wedge-shaped compartments 48 could test for the same property but at different levels of existence of contamination. For example, a first wedge-shaped compartment 48 could be calibrated to indicate a first level of acidity, TCA, brettanomyces yeast, volatile acids, or hydrogen sulfide, and subsequent wedge-shaped compartments 48 could be calibrated to indicate sequentially increasing levels of acidity, TCA, brettanomyces yeast, volatile acids, or hydrogen sulfide. Such an ability could be considered particularly advantageous relative to characteristics, such as brettanomyces yeast, that are desirable in varying levels by different consumers.

Figure 6:
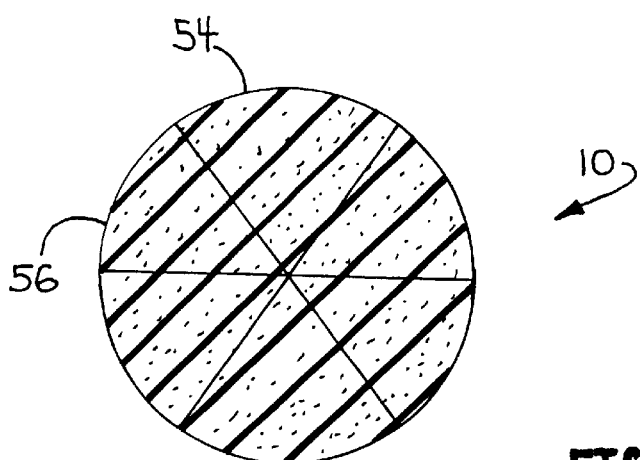
FIG. 6 is a cross-sectional plan view of a still further embodiment of the present invention for a stopper for detecting and indicating fluid properties.

Still another embodiment of the present invention for a stopper for indicating fluid properties is again indicated at 10 in FIG. 6. There, the stopper 10 comprises an essentially unitary body 54 of, for example, cork, a polymer, or any other appropriate stopper material. The body 54 can be considered to be divided into a plurality of wedge-shaped sections 56. Each wedge-shaped section 56 is saturated with a fluid property indicating substance in a manner similar to the embodiment of FIG. 2. With this, the wedge-shaped sections 56 can be employed as the wedge-shaped compartments 48 in FIG. 5 to provide indications of different fluid properties or of different levels of the same fluid property.

Figure 7:
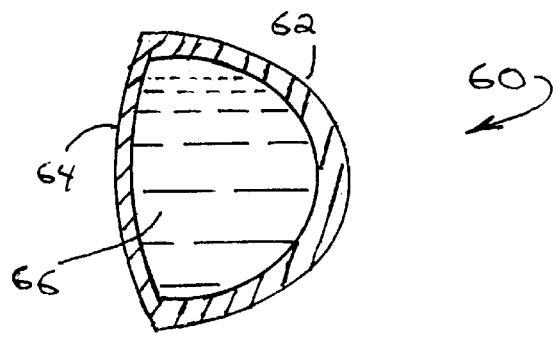
FIG. 7 is a cross-sectional plan view of yet another embodiment of the present invention for a device for detecting and indicating fluid properties.

Yet another embodiment of the invention is indicated generally at 60 in FIG. 7, where it is embodied in a wall-engaging structure. There, the wall-engaging structure 60 has an inner wall 62 and an outer wall 64 that together define an open inner volume that retains a volume of fluid property indicating substance 66. At least a portion of the inner wall 62 comprises a semi-permeable barrier for allowing the fluid property detecting substance 66 to accomplish its purpose of detecting and indicating at least one property of a volume of fluid retained in the bottle relative to which the wall-engaging structure 60 is employed. The outer wall 64 is generally arcuate in cross-section such that it can engage and be secured to a wall portion of a bottle by, for example, adhesive. Preferably, at least a portion of the outer wall 64 is transparent for enabling a user to view the color condition of the fluid property detecting substance 66. Under such an embodiment, the wall-engaging structure 60 can be secured within a bottle to provide a user with a ready indication of a property, such as a level of acidity, TCA, brettanomyces yeast, volatile acids, or hydrogen sulfide, of a fluid retained within the bottle.

From the foregoing, it will be clear that the present invention has been shown and described with reference to certain preferred embodiments that merely exemplify the broader invention revealed herein. Certainly, those skilled in the art can conceive of alternative embodiments. For instance, those with the major features of the invention in mind could craft embodiments that incorporate those major features while not incorporating all of the features included in the preferred embodiments.

With the foregoing in mind, the following claims are intended to define the scope of protection to be afforded the inventor, and the claims shall be deemed to include equivalent constructions insofar as they do not depart from the spirit and scope of the present invention. A plurality of the following claims may express certain elements as a means for performing a specific function, at times without the recital of structure or material. As the law demands, these claims shall be construed to cover not only the corresponding structure and material expressly described in the specification but also equivalents thereof.

What is claimed is:

1. A device for detecting and providing an indication regarding one or more properties of a fluid retained in a bottle, the device comprising:
    a body member;
    a means for retaining the body member relative to the bottle; and
    a fluid property detecting substance operably associated with the body member for detecting and providing an optical indication regarding one or more properties of the fluid retained in the bottle;
    wherein the body member of the device has an open inner volume, wherein the fluid property detecting substance is disposed within the open inner volume of the body member, and wherein the body member has a wall portion that comprises a semi-permeable barrier and wherein the semi-permeable barrier and the fluid property detecting substance are calibrated to allow fluid retained in the bottle to enter the open inner volume of the body member for a detection of the one or more fluid properties but to prevent the fluid property detecting substance from exiting the open inner volume to contaminate the fluid retained in the bottle;
    whereby the device can provide an optical indication regarding one or more properties of the fluid retained in the bottle.

2. The device of claim 1 wherein the fluid property detecting substance comprises a substance for detecting cork taint.

3. The device of claim 2 wherein the substance for detecting cork taint comprises a 2, 4, 6 trichloroanisole (TCA) testing substance.

4. The device of claim 2 wherein the substance for detecting cork taint is chosen from the group consisting of 2, 4, 6 trichloroanisole (TCA), guaiacol, geosmin, 2-methylisoborneol (MIB), octen-3-ol, and/o,r octen-3-one detecting substances.

5. The device of claim 2 wherein the substance for detecting cork taint comprises a brettanomyces yeast testing substance.

6. The device of claim 2 wherein the substance for detecting cork taint comprises a hydrogen sulfide testing substance.

7. A device for detecting and providing an indication regarding one or more properties of a fluid retained in a bottle, the device comprising:
    a body member;
    a means for retaining the body member relative to the bottle; and
    a fluid property detecting substance associated with the body member for detecting and providing an optical indication regarding one or more properties of the fluid retained in the bottle wherein the fluid property detecting substance comprises an acid testing substance;
    whereby the device can provide an optical indication regarding one or more properties of the fluid retained in the bottle.

8. The device of claim 7 wherein the acid testing substance comprises a litmus material for providing an optical indication of a level of acidity of the liquid retained in the bottle.

9. A device for detecting and providing an indication regarding one or more properties of a fluid retained in a bottle, the device comprising:
    a body member;
    a means for retaining the body member relative to the bottle; and
    a fluid property detecting substance operably associated with the body member for detecting and providing an optical indication regarding one or more properties of the fluid retained in the bottle;

whereby the device can provide an optical indication regarding one or more properties of the fluid retained in the bottle;

wherein the body member comprises a stopper with a generally cylindrical body portion for being disposed in a neck portion of the bottle wherein the body member has first and second end walls, an outside wall, and an open inner volume and wherein the fluid property detecting substance is disposed within the open inner volume of the body member; and wherein the open inner volume of the body member is disposed in communication with the second end of the body member, wherein the second end wall comprises a semi-permeable barrier, and wherein the semi-permeable barrier and the fluid property detecting substance are calibrated to allow fluid retained in the bottle to enter the open inner volume of the body member for a detection of the one or more fluid properties but to prevent the fluid property detecting substance from exiting the open inner volume to contaminate the fluid retained in the bottle.

10. The device of claim 9 wherein the generally cylindrical body portion comprises a first annular segment that is coupled to a second annular segment by a tubular member.

11. The device of claim 10 further comprising a plurality of annular fins project from the tubular member for providing an improved seal between the body member and the neck portion of the bottle.

12. A device for detecting and providing an indication regarding one or more properties of a fluid retained in a bottle, the device comprising:

a body member;

a means for retaining the body member relative to the bottle; and a fluid property detecting substance operably associated with the body member for detecting and providing an optical indication regarding one or more properties of the fluid retained in the bottle;

whereby the device can provide an optical indication regarding one or more properties of the fluid retained in the bottle;

wherein the body member comprises a stopper with a generally cylindrical body portion for being disposed in a neck portion of the bottle wherein the body member has first and second end walls and an outside wall and wherein the stopper is impregnated with the fluid property detecting substance.

13. The device of claim 12 wherein the stopper is formed from cork.

14. The device of claim 12 wherein the stopper is formed from a polymeric material.

15. A device for detecting and providing an indication regarding one or more properties of a fluid retained in a bottle, the device comprising:

a body member;

a means for retaining the body member relative to the bottle; and a fluid property detecting substance operably associated with the body member for detecting and providing an optical indication regarding one or more properties of the fluid retained in the bottle;

whereby the device can provide an optical indication regarding one or more properties of the fluid retained in the bottle;

wherein the body member comprises a stopper with a generally cylindrical body portion for being disposed in a neck portion of the bottle wherein the body member has first and second end walls and an outside wall and wherein the stopper comprises a body portion coupled with a property indicating member.

16. The device of claim 15 wherein the property indicating member has an open inner volume and wherein the fluid property detecting substance is disposed within the open inner volume of the property indicating member.

17. The device of claim 16 wherein the property indicating member has an end wall that comprises a semi-permeable barrier and wherein the semi-permeable barrier and the fluid property detecting substance are calibrated to allow fluid retained in the bottle to enter the open inner volume of the body member for a detection of the one or more fluid properties but to prevent the fluid property detecting substance from exiting the open inner volume to contaminate the fluid retained in the bottle.

18. The device of claim 17 further comprising a plurality of retaining prongs that project from the property indicating member from an end wall of the property indicating member opposite the end wall that comprises the semi-permeable barrier such that the plurality of retaining prongs can be embedded in the body portion to couple the property indicating member thereto.

19. A device for detecting and providing an indication regarding one or more properties of a fluid retained in a bottle, the device comprising:

a body member;

a means for retaining the body member relative to the bottle; and a fluid property detecting substance operably associated with the body member for detecting and providing an optical indication regarding one or more properties of the fluid retained in the bottle;

whereby the device can provide an optical indication regarding one or more properties of the fluid retained in the bottle;

wherein the body portion of the device is divided into a plurality of sections wherein each section is impregnated with a fluid property indicating substance that is calibrated to test for and indicate a different property of the fluid retained by the bottle.

20. The device of claim 19 wherein the open inner volume is divided into a plurality of wedge-shaped compartments wherein each wedge-shaped compartment retains a volume of fluid property indicating substance.

21. The device of claim 20 wherein the fluid property indicating substance of each of the plurality of wedge-shaped compartments is calibrated to test for and indicate a different property of the fluid retained by the bottle.

* * * * *